US006503478B2

(12) United States Patent
Chaiken et al.

(10) Patent No.: US 6,503,478 B2
(45) Date of Patent: *Jan. 7, 2003

(54) CHEMICALLY SPECIFIC IMAGING OF TISSUE

(75) Inventors: Joseph Chaiken, Fayetteville, NY (US); Charles M. Peterson, Potomac, MD (US)

(73) Assignee: LighTouch Medical, Inc., New Hope, PA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/482,413

(22) Filed: Jan. 13, 2000

(65) Prior Publication Data

US 2002/0041848 A1 Apr. 11, 2002

Related U.S. Application Data

(60) Provisional application No. 60/115,740, filed on Jan. 13, 1999.

(51) Int. Cl.[7] .................... A61K 51/00; A61M 36/14
(52) U.S. Cl. .............. 424/9.1; 424/1.49; 424/1.11; 356/301
(58) Field of Search .............. 424/1.11, 1.49, 424/1.61, 1.65, 9.1; 423/644; 356/300, 301

(56) References Cited

U.S. PATENT DOCUMENTS

| | | | |
|---|---|---|---|
| 3,849,458 A | * 11/1974 | Dinh-Nguyen et al. | ..... 260/413 |
| 4,893,627 A | 1/1990 | Kehayias et al. | |
| 5,042,488 A | 8/1991 | Ackerman | |
| 5,167,948 A | * 12/1992 | Wenzel | ..... 424/1.11 |
| 5,261,410 A | 11/1993 | Alfano et al. | |
| 5,510,894 A | 4/1996 | Batchelder et al. | |
| 5,932,562 A | 8/1999 | Ostlund, Jr. | |

FOREIGN PATENT DOCUMENTS

| | | |
|---|---|---|
| CA | 1078865 | 6/1980 |
| EP | 0 351 919 | 1/1990 |
| EP | 0 818 674 | 1/1998 |
| WO | WO 92/15008 | 9/1992 |
| WO | WO 93/00856 | 1/1993 |
| WO | WO 96/03074 | 2/1996 |

OTHER PUBLICATIONS

Eskey, Clifford J. et al., "²H–Nuclear Magnetic Resonance Imaging of Tumor Blood Flow: Spatial and Temporal Heterogeneity in a Tissue –isolated Mammary Adenocarcinoma," Cancer Research, Nov. 1, 1992, vol. 52, pp. 6010–6019, XP000999180.
Furuya, Yoshimi et al., "The Measurement of Blood Flow Parameters with Deuterium Stable Isotope MR Imaging," Annals of Nuclear Medicine, 1997, vol. 11, No. 4, pp. 281–284, XP001000595.
Obata, Takayuki et al., Deuterium Magnetic Resonance Imaging of Rabbit Eye in Vivo, Magnetic Resonance in Medicine, Apr. 1995, vol. 33, No. 4, pp. 569–572, XP001000627.
Obata, Takayuki et al., "Noninvasive Analysis of Water Movement in Rat Testis Using Deuterium M agnetic Resonance Imaging," Magnetic Resonance Imaging, 1996, vol. 14, No. 1, pp. 115–119, XP001000611.
R.R. Anderson et al. (1981) Journal of Investigative Dermatology, 77:13–19.
K.G. Brown et al. (1973) Biochem. Biophys. Res. Commun. 54:358–364.
E.A. Carter et al. (1998) SPIE 3257:72–77.
H.G.M. Edwards et al. (1996) Chemistry in Australia pp. 454–455.
H.G.M. Edwards et al. (1995) Journal of Molecular Structure 347:379–388.
K. Larsson (1973) Chem. Phys. Lipids 10:165–176.
E.E. Lawson et al. (1997) Journal of Raman Spectroscopy 28:111–117.
R. Mendelsohn et al. (1976) "Deuterated Fatty Acids as Raman Spectroscopic Probes of Membrane Structure," Biochim. Biophys. Acta 443(3)613–617.
M. Rajadhyaksha et al. (1995) Journal of Investigative Dermatology, 104(6):946–952.
S. Sunder et al. (1976) "Raman Studies of the C–H and C–D Stretching Regions in Stearic Acid and Some Specifically Deuterated Derivatives," Chem. Phys. Lipids 17(4):456–465.
Y. Furuya et al., 1997, "The measurement of blood flow parameters with deuterium stable isotope MR imaging," Annals of Nuclear Medicine, 11(4):281–284.
T. Obata et al., 1995, "Deuterium Magnetic Resonance Imaging of Rabbit Eye in Vivo," XP–001000627, MRM 33:569–572.
T. Obata et al., 1996, "Noninvasive Analysis of Water Movement in Rat Testis Using Deuterium Magnetic Resonance Imaging," XP–001000611, Magnetic Resonance Imaging, 14(1):115–119.
C.J. Eskey et al., 1992, "²H–Nuclear Magnetic Resonance Imaging of Tumor Blood Flow: Spatial and Temporal Heterogeneity in a Tissue–isolated Mammary Adenocarcinoma[1]," XP–000999180, Cancer Research, 52:6010–6019.

* cited by examiner

Primary Examiner—Dameron L. Jones
(74) Attorney, Agent, or Firm—Gates & Cooper LLP

(57) ABSTRACT

Disclosed are methods and materials for obtaining spatially resolved images of specific types of tissues. The method for imaging tissue comprises administering to the tissue a deuterated imaging agent and performing spectroscopy, preferably Raman spectroscopy. Electromagnetic radiation, such as a near infrared laser beam, is directed to a tissue of interest. The radiation can be scanned across and within the tissue of interest. When used in combination with a light collection system, it is possible to map out a specific volume of tissue, obtaining information regarding the distribution of specific endogenous chemical species. In some embodiments, specific imaging agents are employed to impart contrast between chemically different types of tissues.

40 Claims, 11 Drawing Sheets

CHEMICALLY SPECIFIC IMAGING OF TISSUE

This application claims the benefit of United States provisional patent application serial No. 60/115,740, filed Jan. 13, 1999, the entire contents of which are incorporated herein by reference. Throughout this application, various publication are referenced. These publications are incorporated herein by reference in order to describe more fully the state of the art to which the invention pertains.

TECHNICAL FIELD OF INVENTION

The invention relates to a method for noninvasive imaging of skin and other tissues using spectroscopy. The invention relates to administering a deuterated imaging agent to a tissue of interest prior to spectroscopic probing. Chemically specific imaging can be achieved by use of specific imaging agents.

BACKGROUND OF THE INVENTION

There is a need for reliable and precise methods for diagnosing medical abnormalities and for assessing the general condition of body tissues. While any approach that offers early and reliable warning of medical problems has some utility, noninvasive methods offer many advantages. Anticipation by a patient of pain and scarring associated with invasive procedures can cause delays in seeking medical attention. There is also a myriad of inconveniences, risks and difficulties associated with direct collection and contact with patient body fluids. For these reasons, there has been intense scientific and engineering research into devising noninvasive approaches to assessment and diagnosis of medical conditions.

Use of spectroscopic methods, while of considerable use in direct in vitro application to fluids, has not found equal in vivo application. In vivo sampling is substantially more complicated for a variety of reasons, although some of the challenges can be handled by reference to in vitro procedures. Even in vitro procedures require at least some sample preparation before spectroscopic interrogation. And in vivo samples cannot be handled with nearly the ease of in vitro samples.

All chemometric analyses benefit from the availability of samples having known composition of various analytes and having favorable light propagation properties, allowing a straightforward application of Beer's law. Selectively modulated in vitro samples, or "exemplars", are much easier to synthesize or otherwise obtain than in vivo exemplars. Thus, samples for chemometric interpretation of in vivo samples can be expected to require specialized approaches to sample preparation and specifically designed methods for obtaining modulated samples of known composition.

Perhaps the most important approach to detecting tissue abnormalities is by direct observation. This requires specialized stains to produce images and in this regard, there is considerable ongoing research. Neither magnetic resonance, radioactive tracers nor fluorescent imaging agents are ideal for in vivo applications because the former lacks sufficient spatial resolution and the latter two have potential toxicity problems.

Long data collection times are needed to extract small signals from some samples, but in vivo sampling requires the patient to endure the waiting. Prolonged data collection is not always practical. Moreover, applying too much excitation light to in vivo samples can lead to catastrophic results. Thus, there remains a need for non-invasive methods for producing spatially resolved images of living tissues.

SUMMARY OF THE INVENTION

To address the above-described needs, the invention provides methods and materials for obtaining spatially resolved images of specific types of tissues. In a preferred embodiment, the method for imaging tissue comprises administering to the tissue a deuterated imaging agent and performing spectroscopy, preferably Raman spectroscopy. Electromagnetic radiation, such as a near infrared laser beam, is directed to a tissue of interest. The radiation can be scanned across and within the tissue of interest. When used in combination with a light collection system, it is possible to map out a specific volume of tissue, obtaining information regarding the distribution of specific endogenous chemical species through the imaging of exogenously applied deuterated agents. In some embodiments, specific imaging agents are employed to impart contrast between chemically and physically different types of tissues.

In one embodiment, the analyzing comprises determining a surface fractal dimension of a portion of the tissue having an area and a perimeter. Given suitable images, determining surface fractal dimension involves determining the scaling of the area with the perimeter. This scaling can be measured using a "box counting" procedure from a single image or directly measured using several images obtained on different spatial scales. The method of determining a surface fractal dimension can comprise dividing the area of the portion of tissue by the perimeter of the portion of tissue. It is also possible to obtain a fractal dimension for non-closed loops (e.g., cracks, masses having indistinct borders), also using box counting. The portion of tissue can be a cell, a mass of cells or a tumor.

In another embodiment, a surface fractal dimension is derived from first and second iterations of irradiating the tissue and collecting and analyzing spectra emitted by the tissue. These iterations are performed with first and second regions of the tissue, respectively, wherein the first region of the tissue comprises a portion of the second region of the tissue. The analyzing can then further comprise comparing a quantity of Raman spectra emitted by the first and second regions of the tissue. In one embodiment, the comparing comprises determining a slope of a line connecting first and second points, wherein the first point is a logarithm of total Raman spectra emitted by the first region of the tissue plotted as a function of a logarithm of area of the first region of the tissue, and the second point is a logarithm of total Raman spectra emitted by the second region of the tissue plotted as a function of a logarithm of area of the second region of the tissue. In this manner, multiple regions (e.g., first, second, third, fourth regions, etc.) of overlapping portions of tissue can be probed and analyzed to obtain a surface fractal dimension.

In preferred embodiments, a class of Raman specific agents is employed. The invention provides deuterated imaging agents that are suitable for use with Raman spectroscopy. The general class includes, but is not limited to, water, organic solvents, phospholipids, simple alkyl esters, long chain alkyl esters, long chain alkyl alcohols, fatty acids, urea and its derivatives, and pyrrolidones. Within this general class are preferred compounds such as partially deuterated and perdeutero- {stearic acid, palmitic acid, linoleic acid, oleic acid, mono-, di- and tri-glycerides and glycerol, cholesterol, propylene glycol, 1–8 cineol, 2-n-nonyl-1,3-dioxolane (U.S. Pat. No. 4,861,764), 1-dodecylazacycloheptan-2-one (AZONE), and 4-decycloxazolidin-2-one PERMAC SR-39), and ceramides 1–6: sphinganine, 4-hydroxysphinganine, N-acetylated sphinganine and N-acetylated 4-hydroxysphinganine (N-acetylated by different fatty acids)}. The degree of deuteration of the imaging molecule need not be exhaustive, such that one can balance the ease of obtaining a particular isotopic substitution against the sensitivity and selectivity afforded by that particular molecule. The method can be executed with spatial resolution well below 100 microns (e.g., 5–10 microns), and can provide meaningful information on a one-second time scale. Expect for the use of a benign imaging agent, the method can be performed non-invasively.

In preferred embodiments, the tissue of interest is skin. The tissue can be finger tip, ear lobe, neck, back, leg, arm, shoulder, or other skin regions of interest. Other tissues can be used, including, but not limited to, biopsied tissue and deep tissues accessed surgically. The tissue can be living or dead. Preferably, the tissue is human, or of other mammalian origin.

DETAILED DESCRIPTION OF THE INVENTION

Figure 1:
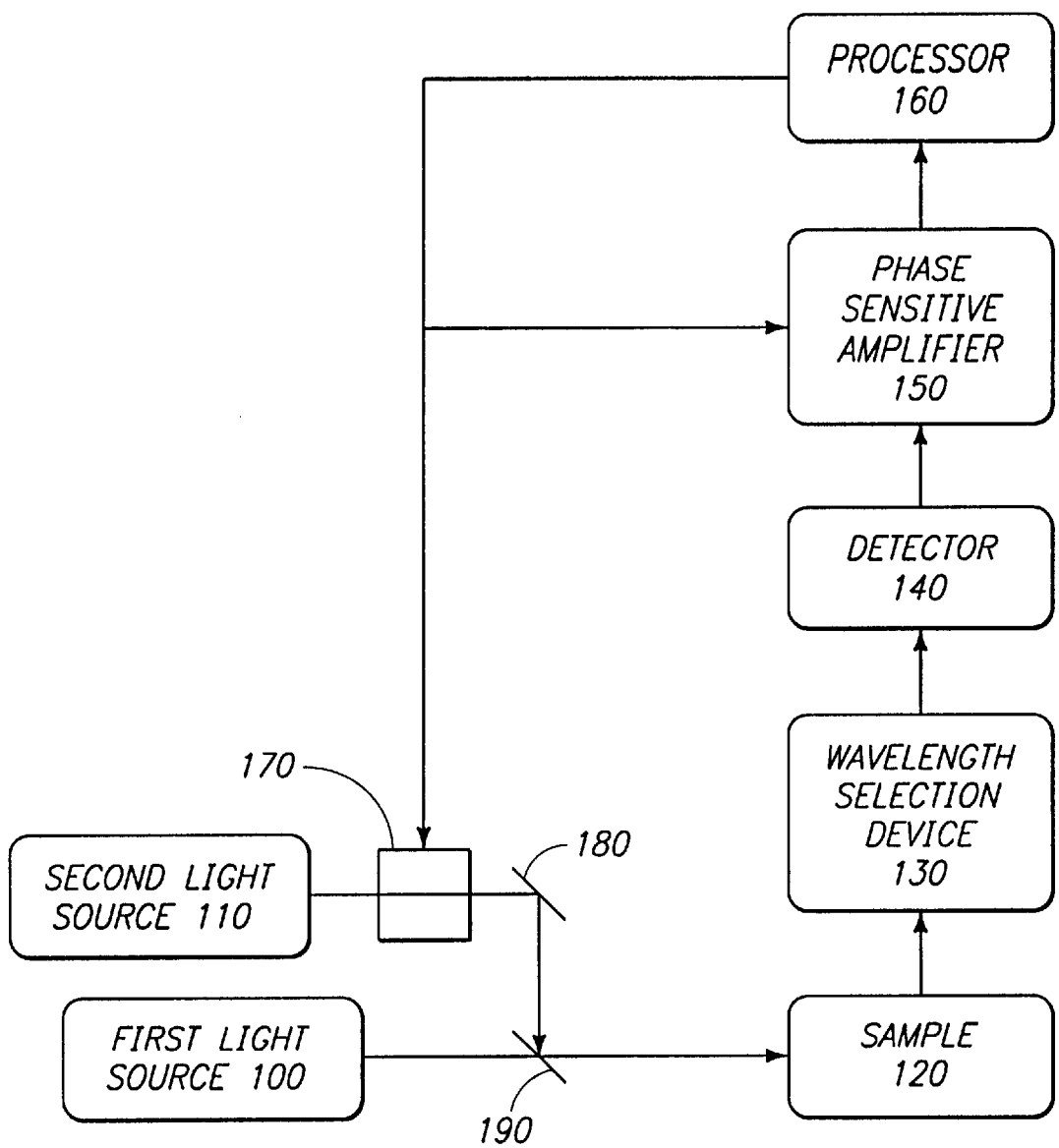
FIG. 1 is a block diagram representing one embodiment of an apparatus for use in accordance with the invention.

The present invention is based on the discovery that deuterated imaging agents can be used to obtain distinct spectroscopic signals from deep as well as superficial portions of living tissue. Recent improvements in lasers, computers and light detection instrumentation have made quantitative in vivo Raman spectroscopy of human tissue, and particularly human skin, a reality. Other tissues, employing invasive as well as noninvasive approaches can be imaged using the process and materials taught herein, however, the invention will first be described in the context of skin. A considerable amount of Raman scattering from C—H bonds and O—H bonds has been observed. In either case, substituting a deuterium for a hydrogen results in a lowering of the vibrational frequency by a factor of about 1.414, into a range typically devoid of other spectroscopic features. This dramatic shift, about 800to 900 $cm^{-1}$ for C—H bonds and about 900–1000 $cm^{-1}$ for O—H bonds, coupled with the fact that there are inherently very few other Raman features in the same spectral regions, is particularly advantageous.

Definitions

All scientific and technical terms used in this application have meanings commonly used in the art unless otherwise specified. As used in this application, the following words or phrases have the meanings specified.

As used herein, "deuterated imaging agent" refers to a substance comprising deuterium that is capable of being administered to a tissue.

As used herein, "administering" includes topical, systemic, and parenteral (including, e.g., intravenous) modes of administering an agent to a tissue.

As used herein, a "highly penetrating imaging agent" is one that will continue to be detectable via spectra emitted by the tissue after repeated washing, such as after two or more acetone rinses, and penetrates tissue to a depth at least as great as the depth of penetration of a light source used for spectroscopic probing of the tissue (approximately 2–3 mm).

As used herein, "antibody" refers to both monoclonal and polyclonal antibodies. Also included are modified antibodies, such as chimeric or humanized antibodies.

As used herein, a "fragment" of an antibody means a portion of an antibody that retains the ability to specifically recognize and bind an epitope. Examples of such fragments include Fab, F(ab')2, Fv or Sfv fragments as well as recombinant proteins comprising the antigen binding region of a monoclonal antibody.

As used herein, "Raman spectra associated with" a given component refers to those emitted Raman spectra that one skilled in the art would attribute to that component. One can determine which Raman spectra are attributable to a given component by irradiating that component in a relatively pure form, and collecting and analyzing the Raman spectra emitted by the component in the relative absence of other components. Those skilled in the art are aware of available libraries that catalog known Raman spectra.

As used herein, to "enhance a target signal" means to increase the quantity or quality of a target signal having a wavelength associated with an analyte of interest relative to the quantity or quality of a non-target signal having a wavelength not associated with the analyte of interest, or relative to random noise associated with the measurement process. This enhancement can be either pure signal-to-noise improvement, or enhancement of target signal over background.

As used herein, a "strong" feature is a Raman feature that results in one scattered wavelength-shifted photon per $10^4$–$10^6$ incident excitation photons. Where the Raman features have been resonance enhanced or surface enhanced, strong features can result in one scattered wavelength-shifted photon per $10^3$–$10^6$ incident excitation photons.

As used herein, a "weak" feature is a Raman feature that results in one scattered wavelength-shifted photon per $10^8$–$10^9$ incident excitation photons.

As used herein, "wavelength dispersion" means spatially separating signals of individual wavelengths within a group of wavelengths. Such dispersion can be achieved with, for example, a spectrograph or use of one or more filters.

As used herein, "tissue" means any portion of an organ or system of the body, including, but not limited to, skin, capillary beds, blood, muscle, breast and brain.

As used herein, unless context clearly indicates otherwise, "a" or "an" means at least one, and can include a plurality.

Deuterated Imaging Agents of the Invention

The invention provides deuterated imaging agents. The agents are suitable for use with the methods of the invention and with Raman spectroscopy. Deuterium is a nonradioactive isotope of hydrogen that is virtually identical with the normal isotope with regard to chemical properties.

For the purposes of the subject invention, typically doses on the order of a gram or less would be used in a one-time exposure. Moreover, the imaging agent can be applied on a topical basis. If administered by ingestion, the total exposure would be far less (by a factor of about a million) from doses that, over a long period of continual usage, will cause the beginnings of observable effects. In addition, deuterium can be incorporated into molecules in non-exchangeable positions in the molecular structure. These molecules are often excreted intact and the deuterium easily cleared from the patient's system naturally.

Deuterium is essentially nontoxic, unless ingested in a continuous regimen of D2O for a period of days. In such a case, there are still no signs of ingestion or poisoning in lab rats until 10–15% of the animal's total body water weight is replaced by the D2O. At about double this exposure, the symptoms become severe. Unless a human subject ingests 10–15 pounds of pure D2O for a week or two, no side effects would be expected.

The general class of agents provided in deuterated form includes, but is not limited to, water, organic solvents, phospholipids, simple alkyl esters, long chain alkyl esters, long chain alkyl alcohols, fatty acids, urea and its derivatives, and pyrrolidones. Within this general class are preferred compounds such as partially deuterated and perdeutero-{stearic acid, palmitic acid, linoleic acid, oleic acid, mono-, di-and tri-glycerides and glycerol, cholesterol, propylene glycol, 1–8cineol, 2-n-nonyl-1,3-dioxolane (U.S. Pat. No. 4,861,764), 1-dodecylazacycloheptan-2-one (AZONE), and 4-decycloxazolidin-2-one (DERMAC SR-39), and ceramides 1–6: sphinganine, 4hydroxysphinganine, N-acetylated sphinganine and N-acetylated 4-hydroxysphinganine (N-acetylated by different fatty acids)}. Preferred agents for deuteration comprise agents in which C—H bonds or O—H bonds with C—D or O—D bonds, respectively, or in which C—H is replaced with C—C—$D_3$ or C—$C_n$—$D_{2n-1}$, or unsaturated versions of the above.

The invention also provides a composition comprising a deuterated imaging agent of the invention, as described above. In one embodiment, the composition is a diagnostic composition. In a preferred embodiment, the composition is for use with Raman spectroscopy. The composition optionally contains a pharmaceutically acceptable carrier. Examples of suitable carriers include, but are not limited to, cyclodextrins and solubilizing agents, such as polyethylene glycols (PEGs) and dimethyl sulfoxide (DMSO).

Raman Spectroscopy of Skin

To perform absorption based vibrational spectroscopy, the use of infrared radiation to obtain quantitative information is limited by the transmission properties of the tissue. There is considerable Mie scattering, spatial inhomogeneity, and tortuous interfaces permeating tissues and organs, making quantitation of path length problematic and complicating the applicability of Beer's Law. Moreover, absorption limits the amount of light that can be employed. The availability of adequate infrared lasers or adequate incoherent light sources is limited. Optical contact with the skin or other tissue can be made using either waveguide, i.e. evanescent wave, or direct contact, and is often difficult to perform reproducibly.

In large part, moisture content of a naturally hydrated biomembrane, such as stratum corneum, makes direct infrared absorption/reflectance spectroscopy problematic, i.e. difficult to execute reproducibly, regardless of how the light contacts the skin. For example, stratum corneum is typically about 10 $\mu$m thick, but can swell to several times that thickness when wet. This variation in density affects light propagation in a way that poses nonlinearity problems. Raman spectroscopy, on the other hand, is much less affected by water, and so is often the method of choice for wet samples.

On the other hand, Raman scattering is a comparatively weak process and, given the peculiar optical properties of human tissue, a novel approach is required to actually obtain meaningful in vivo spectra. There must be control of blood flow, or some type of compensation in the data analysis for whatever form of tissue modulation is employed. Local pressure and temperature can have a dramatic effect on the blood volume of the intersection between the irradiation zone and the collection zone. Described in U.S. patent application Ser. No. 09/456,020, filed Dec. 3, 1999, is a system to maintain focus of the combined excitation and collection systems at the desired position on or within the skin or surrounding tissues. To this end, an approach has been devised to allow a nonimaging optical system to establish a feedback loop and thereby a servo system for maintaining the position and the depth of focus of the Raman excitation source as the sample is moved, as is required for obtaining scanning laser confocal images and Raman microprobe images. The same approach can serve to maintain the optimal configuration of the light collection system as well. The method disclosed in U.S. patent application Ser. No. 09/456,020allows such spectroscopic data to be collected with greater efficiency, greater selectivity, and ultimately, higher signal to noise. The methods and apparatus disclosed therein provide for regulation of lens and aperture positions and excitation wavelength output, as well as for use of spectroscopic depth markers based on Raman features associated with different layers of tissue.

Target spectra for obtaining information about skin and tissue contents have been identified in the literature. Edwards et al., 1995, J. Molecular Structure 347:379–388; and Carter et al., 1998, SPIE 3257:72–77, describe Raman features of interest to dermatological diagnostics. Lawson et al., 1997, J. Raman Spectroscopy 28:111–117 describes Raman spectra associated with cancers, tumors, DNA, stratum corneum, hair and nails. Tu, 1982, Raman Spectroscopy in Biology: Principles and Applications, Chap. 5:134–149, describes Raman features associated with nucleic acids and inorganic phosphate.

Methods of the Invention

The invention provides methods of imaging and methods of diagnosis. In one embodiment, the method comprises administering to a target tissue a deuterated imaging agent. The method further comprises irradiating the tissue with a source of electromagnetic radiation and collecting and analyzing spectra emitted from the tissue.

In preferred embodiments, the spectra collected and analyzed are Raman spectra. In one embodiment, the deuterated imaging agent comprises an agent that specifically recognizes and binds a target tissue. The target tissue can then be identified by collection and analysis of spectra emitted by the deuterated imaging agent. In one embodiment, the agent comprises an antibody or fragment thereof. Other molecules that specifically recognize and bind a target tissue are known in the art.

In another embodiment, the deuterated imaging agent comprises a penetrating agent. The penetrant can be selected so as to be highly penetrating or selectively penetrating. The nature of the penetrant can be selected so as to enhance preferentially imaging of voids or imaging of densified regions, depending on the objective. A highly penetrating imaging agent will continue to be detectable via spectra emitted by the tissue after repeated washing, such as after two or more acetone rinses. A less penetrable tissue, e.g., a densified region, will contain less imaging agent than the surrounding tissues.

In one embodiment, the method can be used to obtain an early diagnosis of cancer or other conditions, including skin cancers and skin conditions. Examples of skin cancers include, but are not limited to, malignant melanoma, squamous cell carcinoma and basal cell carcinoma. In some embodiments, the method comprises administering an antibody or other chemical entity that binds specifically to such tissue or cells of interest. The tissue or cells of interest, or an area of tissue to be scanned, are referred to herein as "target tissue". Examples of target tissues include, but are not limited to, skin and surrounding tissues as well as any tissue or organ accessible for in situ biopsy, such as breast, brain, liver, pancreas, kidney, intestine, etc. Accessibility of tissues is constrained only by the depth of penetration of the laser used. Typical penetration depths range from about 300 microns to about 3000 microns, depending on the excitation wavelength chosen and the type of tissue involved.

The specifically-binding molecule is then modified to contain some deuterium substitution. The molecule can be modified directly by deuterium substitution, or indirectly by attaching a second moiety that is deuterated. One example of a second moiety that can be attached is a long deuterated alkyl chain. This is easily done and is possible for virtually any molecule that contains hydrogen.

The molecule is then spread, sprayed or otherwise placed in contact with the target tissue and allowed to interact (typically for a period ranging from minutes to an hour or two). Any excess material can be washed off, for example, by rinsing the tissue with acetone. A set of Raman spectra are then obtained from the suspected region to assess the presence of deuterium. In preferred embodiments, the deuterium is found in molecules containing carbon as C—H bonds. The portions of tissue emitting such Raman spectral features (e.g., a Raman peak that is associated with deuterium, and that is not found in tissues not treated with deuterated agents) are therefore suspect of being cancerous or precancerous, depending on the type of specificity incorporated into the deuterium bearing imaging agent.

In other embodiments, instead of using an agent that has specific binding properties, an agent having superior penetration properties is used. Agents having superior penetration properties are characterized by having the features of a good transdermal drug delivery vehicle. For example, an agent having superior penetration properties can penetrate $10^2$–$10^3$ microns of skin tissue in $10^{-1}$ minutes or less. Examples of such agents include, but are not limited to, DMSO, PEGs, cyclodextrins, azone, and DERMAC. The imaging agent will become uniformly dispersed throughout the exposed tissues to the extent that the agent is equally soluble in both aqueous and non-aqueous (e.g., lipid-based) media. Scanning this region reveals voids and densified regions, which are incipient wrinkles and cracks that could then be treated with appropriate skin care or cosmetic formulations. Voids are places where deuterated imaging agent will accumulate either inside or along inside boundaries, while densified regions are sites where there is slower penetration and less deuterated agent will be found.

It is also possible to employ an agent that bonds preferentially or specifically to connective tissues that are affected by arthritis and other similar afflictions. Examples of agents for this purpose include, but are not limited to, antibodies to TNF-α and other cytokines, such as the interleukins, which are released at sites of inflammation., In this case, the agent is made to come into contact with the tissue via ingestion (e.g., pill) or via injection into the suspected area. The tissue is then examined noninvasively using Raman spectroscopy in the near infrared spectral range, which will penetrate to such depths in vivo applications. The method provides a positive diagnosis if the deuterium labeled agent is found to be localized in the joints and surrounding regions are suspected of being affected.

In other embodiments, the same approach can be used to obtain a rapid biopsy of tissues being removed during surgery or other invasive procedures. In this case, the imaging agent is applied to the suspected tissues, which are then Raman scanned. If all the affected tissues have been removed, then there will be no binding of the imaging agent to the surgical area and the surgeon can be assured that enough tissue has been removed. The method can be used to obtain information regarding both the excised and remaining tissues.

Tissue Biopsy and Characterization

In many cases, when normal and corresponding cancerous types of cells of a particular type of tissue are viewed using light microscopy, they have a reproducible difference in gross physical appearance. This provides the basis for many conventional, in vitro tissue biopsy protocols in which the tissues must be stained. Similarly, there are a variety of skin and other tissue states that are discriminated on the basis of morphological appearances. Some skin conditions, wrinkles, cracks and voids, are simply skin having a certain physical morphology, while it may or may not have underlying distinct physical manifestations. The ability to discern regions of tissue in which deuterated substances exist, (regardless of how they may have gotten there) in a background of the same or similar substances, but in undeuterated form, provides an environment for using deuterated stains, or "imaging" agents. These agents have specific utility for allowing noninvasive morphological examination of in vivo tissues.

Stains aid in visualization of tissues by combining a distinctive spectral response, e.g. color or Raman features in the present case, which allows easy observation using optical or Raman microscopy, with a preference for binding to specific tissues or cell parts, e.g. membranes or nuclei. In the case of the deuterated stains described in this application, the agent's "distinctive spectral response" takes the form of a strongly shifted Raman spectrum that is easily observed and quantified using conventional Raman microscopic methods. This can be performed either with or without the use of confocal imaging to obtain depth resolution. Lateral and longitudinal spatial resolution of 10 microns is possible, and images corresponding to a depth of penetration of at least several hundred microns are attainable.

A wide variety of deuterated stains, imaging agents and contrast agents can be produced. Chemically deuterated molecules are so similar to undeuterated molecules that, in some cases, deuterated contrast agents could be developed directly from stains that are already in use. Alternatively, deuterated, biologically produced molecules, e.g. antibodies, can be employed. As will be discussed in greater detail elsewhere, those skilled in the art are aware of many other ways to obtain suitable deuterated agents.

There are many ways to use deuterated imaging agents for in vivo or in vitro tissue biopsy, or to observe the morphologies of tissues. In the most basic approach, the agent is applied topically so that it may contact the tissues and be allowed to penetrate via whatever routes are available. Each tissue type has specific characteristics, but the present description is tailored to skin. Those skilled in the art will recognize that the guiding principles contained in the discussion which follows can be applied to other tissue types.

There are a variety of transdermal approaches to drug delivery, and imaging agents can be thought of in much the same way. For example, lipid based materials penetrate the skin initially via the interfaces between the keratinized cells forming the outermost layer(s) of the stratum corneum. Aqueous phase materials can interact with the keratinized cells themselves, in addition to penetrating along the boundaries between such cells. Water, lipid based media and other chemicals, e.g. DMSO, can penetrate to submerged cell membranes and blood vessels at all depths thereby transporting potential imaging agents inside cells and to the surfaces of cells at all depths. Suitable imaging agents are selected so as not to be deactivated by the transporting fluid, and so that the two materials are sufficiently mutually soluble.

Whether a particular agent penetrates a specific cell membrane or not depends of the type of cell and the nature of the imaging agent, but many agents can be brought to the surfaces of cells below the surface, if their solubility is appropriate. Once below the outermost surface of the stratum corneum, there are interfacial regions or spaces extending parallel or perpendicular to the skin surface, between adjacent layers of progressively less and less keratinized cells as one goes deeper into the skin, consisting of lipid-aqueous phase bilayers, i.e. interstitial fluids, which can allow movement of both lipid and aqueous phase reagents.

Deeper still are the epidermis and the capillary bed. Here the so-called "brick and mortar" construction of the stratum corneum no longer exists, and the capillary bed involves a highly convoluted mixture of fluid transport tubes (capillaries, arterioles, venules, etc.) and viable epidermal cells. The epidermal cells give way several layers deeper to the dermis, several hundred microns below the surface of the stratum corneum. It is therefore possible to bring agents to all regions of the tissues with either lipid based, aqueous based or amphiphilic based transdermal reagents.

Wrinkles, cracks, and voids are macroscopic morphological changes that may or may not be accompanied by chemical differences in the tissues. By the time these structures can be observed using the unaided eye, there is little that can be done to prevent either their formation or further growth. Thus one goal is to provide imaging agents that can be used to discern "precracks", "prewrinkles" or "prevoids" so that appropriate preemptive steps can be taken.

In one embodiment of the invention, an imaging agent is applied to a tissue of interest, such as a suspect area of skin. The agent is applied to both the skin in question (referred to as suspect-skin), and to a nearby region that is not suspected of any abnormality (referred to as normal-skin below). Comparing the amount of deuterium related signal that persists after washing the imaging agent off the exposed skin, as well as off the unexposed, normal or control skin region, allows the practitioner to biopsy the suspect skin. To the extent that the reference skin is normal and the suspect skin does not interact with the selectively binding imaging agent, diseased skin is discernable from healthy skin.

For the equation below, the greater the ratio in excess of 1, the greater the chances the tissue is cancerous, for example:

$$\frac{(\text{suspect skin})_{after}/(\text{suspect skin})_{before}}{(\text{normal skin})_{after}/(\text{normal skin})_{before}} > 1.$$

Each parenthesis corresponds to a measurement of a deuteration signal from the agent that binds specifically to certain types of tissues, e.g. a deuterated antibody or other chemically/biologically specific binding agent. Note that the above equation can be used whether the imaging agent reacts chemically, or simply interacts physically (no breakage of hydrogen or other chemical bonds), as in a lipid-based penetrant containing a plethora of C—D bonds. This is important because cell morphology affects surface area of cells, which in turn affects the amount of material that can cling to the cell surface. Cell morphology is useful as an indicator of cell type.

The above approach involves an agent that binds to the affected area, or not, depending on some chemical interaction between the agent and the tissue, which results from the simple binding of one molecule to another. It is also possible that deuterium can be implanted into many tissues on a transient basis (Chaiken et al., 2000, "Noninvasive, in-vivo, near infrared vibrational spectroscopic study of lipid and aqueous phases of skin and near surface tissues," Proc. SPIE, in press). In this case, the amide linkages of proteins can be deuterated by exchange. Many other molecules can be deuterated by exchange of deuterium with protons, e.g. hydroxy groups, keto-enol pairs, and other structures. Combined with tissue modulation to physically move and thereby help distinguish signals that come from mobile tissues, it is possible to map out the degree of deuteration and thereby obtain a map of the static exchangeable protein/amide linkages in the skin and other tissues.

First, inundating a region of skin for 15 minutes to an hour with $D_2O$ or the corresponding physiological saline solution, (the time can be crudely judged in each case by assessing how "pruned" the skin becomes), results in exchange of amide protons with deuterons as shown in the equation below, and the amide III vibration at about 1240 $cm^{-1}$ shifts downward to about 970 $cm^{-1}$.

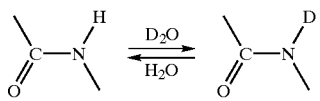

The ratio of appropriately integrated spectral features: (Raman signal at 970 cm$^{-1}$)/(Raman signal at 1240 cm$^{-1}$) = degree of amide deuteration, is a direct measure of the degree of amide deuteration of the region determined by the overlap between the laser excitation zone and the scattered light detection volume. For example, the center cm$^{-1}$ shift can range between about 940 and 980 and between about 1220 and 1270 cm$^{-1}$, respectively. "Appropriately integrated" means integrating at +/− about 12 cm$^{-1}$ on either side of the peak (970 and 1240 cm$^{-1}$, respectively). The spectrum also must be appropriately normalized to account for optical properties of wet tissue. One strategy for normalizing is described in Example 2 below. As the overlap of the two regions is maintained while the tissue is systematically moved, a map of the protein that is capable of exchanging deuterium in the area is obtained.

Regions where water cannot penetrate will reflect no deuteration in any case. Thus densified regions will usually have slow penetration of the deuterant (when it is $D_2O$), thereby leading to a low degree of deuteration as defined above. This provides a means to discern densified regions of in vivo tissue noninvasively. Regions where there are openings and loosening or softening of layers of bricks and mortar, i.e. where there are incipient wrinkles, cracks and voids in the stratum corneum, will have increased penetration and therefore faster and more extensive deuteration, and possibly even accumulation of penetrant/deuterated imaging agent. Thus, by measuring the degree of deuteration of a tissue sample at different spatial locations at different times, thereby mapping out the distribution of either a penetrant itself (usually lipid based with a plethora of C—D bonds), or the result of a reaction with a deuterant (i.e., exchanged amide linkages), defined by either of the two equations above, it is possible to discern the physical state of stratum corneum, epidermis, the regions in and around the capillary bed, the dermis (i.e., the skin as a whole to a depth of 2000 microns at least) and other tissues.

Protein makes up a large part of skin and many other tissues. The ability to selectively image protein makes it possible to view the more rigid structural element of skin. Without any imaging agent, Raman provides a means for determining the amount of tissue in a particular volume. The greater the signal, all other things being equal, the greater the density of the tissue in question. Normal tissue can be expected to have a density that varies from person to person to some extent, but it is well-correlated within the skin of a particular person.

The weakness of the Raman spectrum of water makes it a good delivery vehicle for protons/deuterons. It is also possible that the agent can have a physical interaction, even if there are no chemical changes involved in the formation of incipient cracks etc. All of the structures that are incipient to cracks, voids and wrinkles involve shapes that are different from what existed when the tissues were younger or less stressed. This is also the case in the standard protocols for cancerous tissue biopsy. Morphological changes can therefore be observed and quantified, and then correlated with appropriate independent assessments of tissue type.

Methods of Image Analysis

The invention provides a novel approach to characterizing the physical shapes of objects, obtaining a measure of surface roughness or the tortuosity of boundaries (as in cell membranes and blood vessels). This amounts to measuring various fractal dimension(s) of the skin or other tissue using the images produced by applying the imaging agent and obtaining Raman spectral-spatiotemporal maps. This procedure can be used with any mode of imaging utilizing either endogenous materials or administration of exogenous imaging agents.

In one embodiment, an image is obtained of a region or portion of tissue. The portion of tissue can be a group or mass of cells, a tumor, or a single cell. The image is obtained with sufficient spatial resolution so as to provide substantial detail concerning the shape of the cell membrane or the shape of the colony of cells, or even the shape of the large group of cells taken as a whole. No other form of noninvasive imaging has sufficient spatial resolution to allow this procedure without introducing nuclear or chemically active and possibly toxic agents.

The perimeter and area of the portion of tissue are then calculated. The ratio of the logarithm of the imaged perimeter of the cell or cell group to the logarithm of the area within the cell or the grouping is a function of the tortuosity of the perimeter. Different types of cells and cell groups have a different ratio. Cells of the same type, but having different perimeters and areas, can be plotted on the same graph (i.e., plotting the logarithm of the area as a function of the logarithm of the perimeter produces a straight line plot having a slope equal to the fractal dimension of the cells. This "fractal dimension" of the cell provides a quantitative way of characterizing cells. Three principle strategies can be used. First, one can use the slope of the logarithm of the length measurement of the perimeter plotted as a function of the logarithm of resolution (size of irradiated portion of tissue). Second, one can use the slope of logarithm of the perimeter plotted as a function of the logarithm of the area. Third, one can use the slope of the length measurement as a function of magnification. Box counting can be employed when only a single image is available. For a general reference on these approaches, see "Fractal Models in the Earth Sciences", G. Korvin, Elsevier, Amsterdam, 1992.

This procedure can be performed with regularity for a wide variety of differently shaped objects. This is analogous to what pathologists do in a qualitative fashion. A group of pathologists examine a cell sample independently of each other, note the shapes of the cells (colony, cell mass, other), as well as other parameters (e.g., number of nuclei per cell or staining characteristics), and then compare notes with other members of the group in a protocol designed to eliminate influencing each other. In this way, the subjective nature of their individual visual examinations are combined, preferably in an unbiased manner, to allow an assessment of the health of the cells in question.

The method described herein, which can also be applied to in vitro biopsy as well, using conventional stains and methods, alleviates the subjectivity of the conventional assessment process. The fractal dimension is simply a characteristic of different shaped objects (see Korvin, supra) and can be empirically correlated with different cell types.

Similarly, another approach borrowed from analysis of metal oxides can be applied to obtain a surface fractal dimension of the tissue (see Cote, Proc. Mat. Res. Soc. 495:413–418, 1998). In this case, a Raman spectrum is obtained from a region using a particular diameter of irradiated zone, and a particular value of the watts of incident excitation power per square centimeter (power density) of exposed skin surface. Adjusting the laser power to keep this power density constant, the radius of the exposed region is changed and a new Raman spectrum is obtained. Plotting either the logarithm of a particular Raman signal (e.g., 1667 $cm^{-1}$, 1275 $cm^{-1}$ amide, $CH_2$ deformation), or the sum of features associated with certain materials, as a function of the logarithm of the area in the surface being irradiated, produces a straight line having a slope that is known as the surface fractal dimension of the skin. This is a measure of shape that can be correlated for different types of cells and cell groupings given the type of images made accessible by the availability of deuterated imaging agents and Raman spectroscopy. Calibrations can be made using tissue known to have a particular pathology, such as cancer, and surface fractal dimensions determined for a tissue of interest can be compared to such calibrations.

Apparatus

A diagram representing an apparatus suitable for use with the invention is shown in FIG. 1. The apparatus is suitable for use with the methods of the invention disclosed herein. Suitable components and specific embodiments of the apparatus can be adapted from other Raman spectroscopy systems known in the art (see, e.g., U.S. Pat. Nos. 5,553,616; 5,510,894; 5,615,673; and 5,551,422).

The first light source 100 emits electromagnetic radiation having a first excitation wavelength. Preferably, the light source is a laser. Examples of lasers suitable for use in producing the first excitation wavelength include, but are not limited to, diode lasers with or without an external cavity, OPO, dye and solid state lasers (e.g., YAG, Alexandrite). In an optional embodiment, the apparatus further comprises a second light source 110 that emits electromagnetic radiation having a second excitation wavelength. Examples of lasers suitable for use in producing the second excitation wavelength include, but are not limited to, OPO, dye, argon ion, krypton ion and frequency-doubled YAG lasers. In one embodiment, the first excitation wavelength is about 632 to about 1100 nm, and the second excitation wavelength is about 0.55–0.4, 0.98, 1.41, 1.89, 2.15, or about 9 to about 11 $\mu$m.

The laser 100 or 110 can be a 785 nm, amplitude and wavelength stabilized, external cavity, CW laser 500, (SDL XC-30; SDL Inc., San Jose, Calif.) or similar laser such as a PI-ECL-785-1000FHP (Process Instruments, Inc., Salt Lake City, Utah), producing a maximum total power of 300–700 mW. In the case of the SDL laser, more than half of this power is associated with a large, spectrally wide and unsymmetrical base of amplified spontaneous emissions (ASE). This is adequate to obtain Raman spectra of simple, less challenging samples, i.e. virtually any in vitro sample. To obtain acceptable in vivo spectra, however, a substantial amount of the ASE should be removed. This is done using a holographic bandpass filter (aiser Optical Systems, Ann Arbor, Mich.). While this does not remove all of the disturbing background radiation, it is adequate to allow in vivo spectra to be obtained. Alternatively, ASE can be removed by using a dielectric filter (Omega Optical, Brattleboro, VT.; CVI, Tucson, Ariz.). The Process Instruments laser contains much less ASE, and so a dielectric filter is adequate to allow in vivo Raman signals to be observed.

Light emitted by the sample 120 enters a wavelength selection device 130. In one embodiment, the wavelength selection device 130 is a spectrograph. The spectrograph can be a Holospec (Kaiser Optical Systems, Ann Arbor, Mich.) or other available spectrograph (e.g., from Process Instruments, Salt Lake City, Utah). The resolution of the spectrograph system is 6 $cm^{-1}$, with wavenumber accuracy of 6 $cm^{-1}$ using a calibration based on known lines in atomic emission spectra. Scattered light can be pre-filtered prior to entering the spectrograph slit using a holographic notch filter. At the center of the band blocking, the optical density is 6 or greater. In one embodiment, the filter has a band blocking width of about 250 $cm^{-1}$ (or about 1 nm), centered at the corresponding excitation wavelength. Outside the band blocking width, the transmission is 90% or greater.

Light of selected wavelengths then passes to a detector 140. The detector 140 is a photosensitive device that is disposed to receive Raman spectra, preferably utilizing charge coupled device (CCD) array detection or microbolometer array (Raytheon, Santa Barbara, Calif.). For example, the detector 140 can comprise an IR enhanced, liquid nitrogen cooled CCD array (LN/CCD-1024EHRB/1, Princeton Instruments, Inc., Trenton, N.J.).

In another embodiment, the detector 140 is a single channel detector. Examples of a single channel detector include, but are not limited to, a photodiode such as an avalanche photodiode, and a photomultiplier tube. Light entering the single channel detector 140 can be filtered, for example, using a holographic bandpass filter or dielectric stack. In preferred embodiments, the detector 140 is cooled using, for example, liquid nitrogen or another suitable cooling method known in the art. The detector 140 produces output signals representative of the Raman spectra scattered by the sample in response to irradiation with the first and/or second light sources 100, 110.

Output from the detector 140 can pass to a phase sensitive amplifier 150 (discussed further below), whose output is passed on to a processor 160. Standard computer equipment can be used for the processor 160 (e.g., parallel, serial, interface cards, A/D and D/A converters), which can include a signal analyzer. In one embodiment, the processor 160 is a computer coupled to receive the output signals produced by the detector 140. The computer 160 processes the output signals to derive a value indicative of the concentration of analyte in the tissue. In one embodiment, the computer 160 processes the output signals in the manner described in U.S. patent application Ser. No. 09/191,478, filed Nov. 12, 1998, and entitled "Method for Noninvasive Measurement of an Analyte", the entire contents of which are incorporated herein by reference.

Signal Modulation

In one embodiment, light emitted by the second light source 110 passes through an amplitude modulator 170 to first and second reflectors 180, 190 such that the light joins the path of light emitted by the first light source 100. The light then irradiates the sample 120. Light scattered by the sample in response to the first light source 100 reaches a wavelength selection device 130 that includes a filter tuned to transmit a selected Raman feature. One such feature includes wavelengths of 1008 nm to 1029 nm for skin keratin excited with 785 nm. In one embodiment, the wavelength selection device 130 has a 250 $\mu$m slit and uses a holographic transmission grating. Selected wavelengths are then received by the detector 140.

The signal from the detector 140 then passes to a phase sensitive amplifier 150 that comprises a lock-in amplifier/gated integrator set to demodulate the signal stimulated by light passing through modulator 170. The processor 160 then takes analog demodulated signal from the phase sensitive amplifier 150 and performs digitization, storage and data processing. In addition, the processor 160 can provide synchronization with concurrent tissue modulation or spatial encoding.

Depth Discrimination

Figure 2:
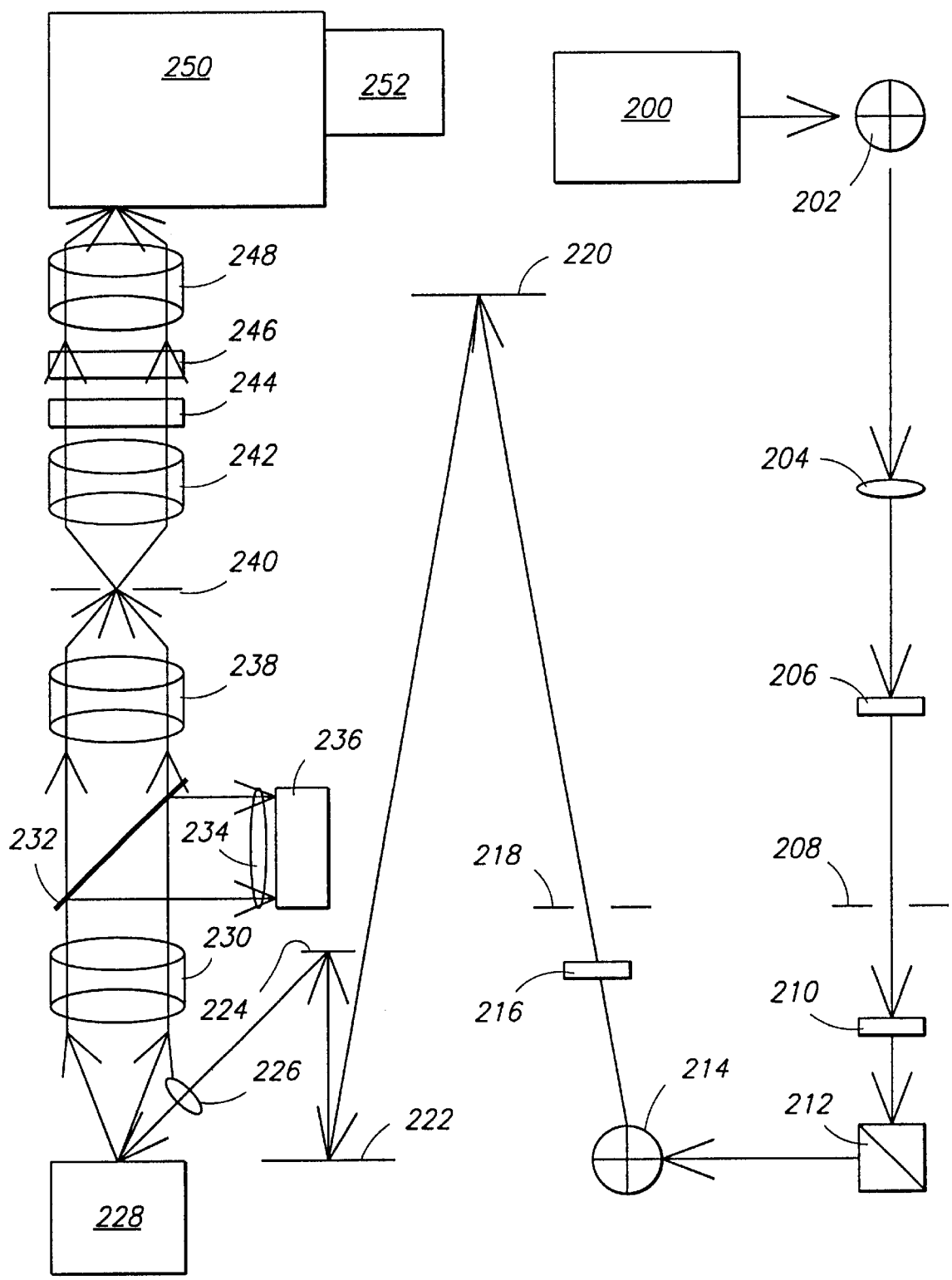
FIG. 2 is a schematic representation of a simple confocal, four-lens system for combining depth discrimination with spectroscopy.

FIG. 2 shows a schematic representation of a confocal, four-lens system adapted for depth discrimination. Such a system can be used to determine the depth of a signal emitted by tissue that is spectroscopically probed. Determination of the depth of a source of emitted light permits identification of the type of tissue, e.g., skin, blood, and of the type of lipid, e.g., lipid, phospholipid, sphingolipid. Lenses 242 and 248 can be matched for their numbers to be appropriate for spectrograph 250, including slit width, and to allow for use of magnification or adjustment of total field of view. The size and position of aperture 240 are chosen to select the depth from which the image is taken and to adjust the longitudinal resolution of the system. As such, the aperture 240 can be on a motorized translation stage, allowing motion in the x, y and z axes.

With reference to FIG. 2, light is directed from a laser source (SDL-XC30) 200 to a periscope 202, then through a 4 meter lens 204, a half-wave plate 206, in iris 208, a metal/dielectric filter 210, a holographic bandpass filter 212, a second periscope 214, a second half-wave plate 216, a second iris 218, a series of three mirrors 220, 222, 224, and a focusing lens 226, before arriving at the tissue, which is positioned in the sample holder 228 (tissue modulation device). Light emitted by the tissue passes through a camera lens 230 and on to a pellicle 232, which directs some of the light to a CCD imaging camera 236 after passing through a lens 234. The remaining light from the tissue is directed through a second camera lens 238, a confocal iris 240, a third camera lens 242, a polarizer 244, a holographic notch filter 246, and a fourth camera lens 248, before the light enters the holographic spectrograph 250 having a light collection efficiency of f=1.4, to which is coupled a CCD detector 252.

Additional options for wavelength stabilization and use of focusing and collection lenses to optimize the spectroscopic measurements are described in U.S. Pat. application Ser. No. 09/456,020, filed Dec. 3, 1999, and entitled, "Method and Apparatus for Noninvasive Assessment of Skin Condition and Diagnosis of Skin Abnormalities", the contents of which are incorporated herein by reference.

EXAMPLES

The following examples are presented to illustrate the present invention and to assist one of ordinary skill in making and using the same. The examples are not intended in any way to otherwise limit the scope of the invention.

Example 1

Penetration and Detection of Stearic-$d_{35}$ Acid

This Example demonstrates the application of a deuterated imaging agent to skin. The Example further demonstrates the feasibility of collecting and analyzing Raman spectra emitted by skin irradiated with a light source, and shows the resulting peaks following application of control and deuterated imaging agents.

Figure 3:
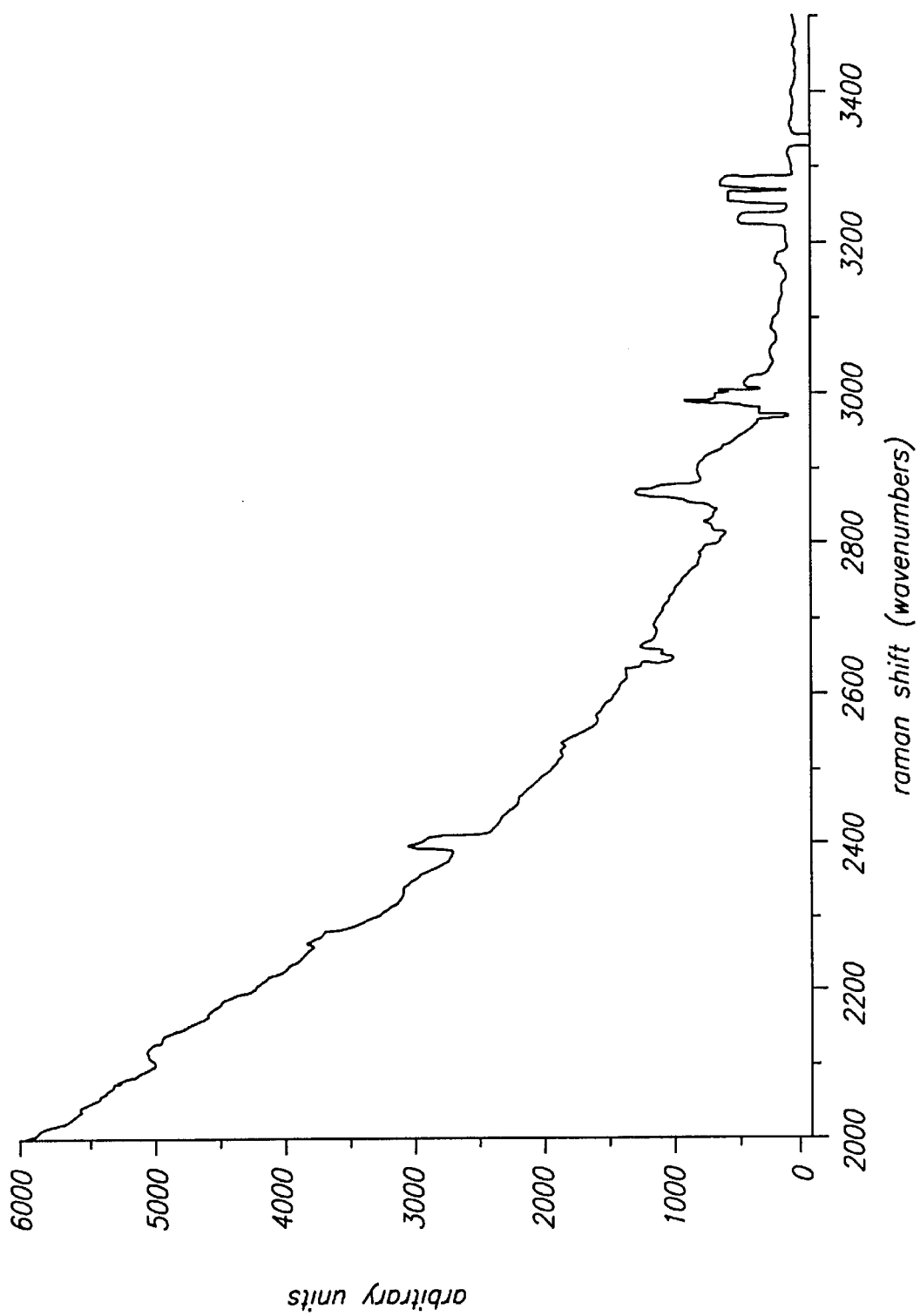
FIG. 3 shows net spectra collected from a human fingertip before and after rinsing the finger tip with acetone, in the absence of application of a test agent.
Figure 4:
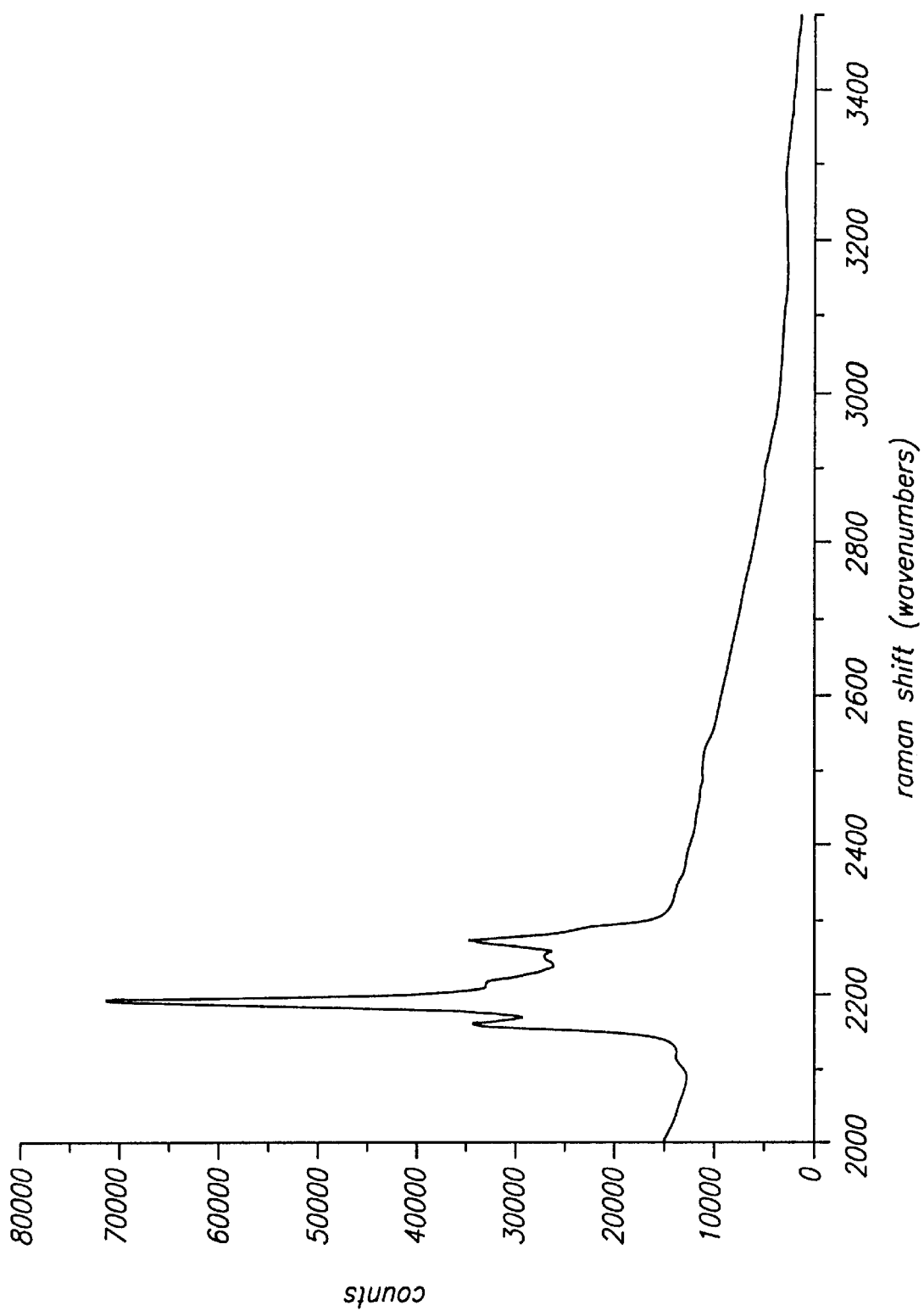
FIG. 4 shows spectra collected from a human fingertip after application of stearic acid-$d_{35}$, without acetone rinsing. The spectra reveal a distinct peak at a Raman shift near 2200 $cm^{-1}$.
Figure 5:
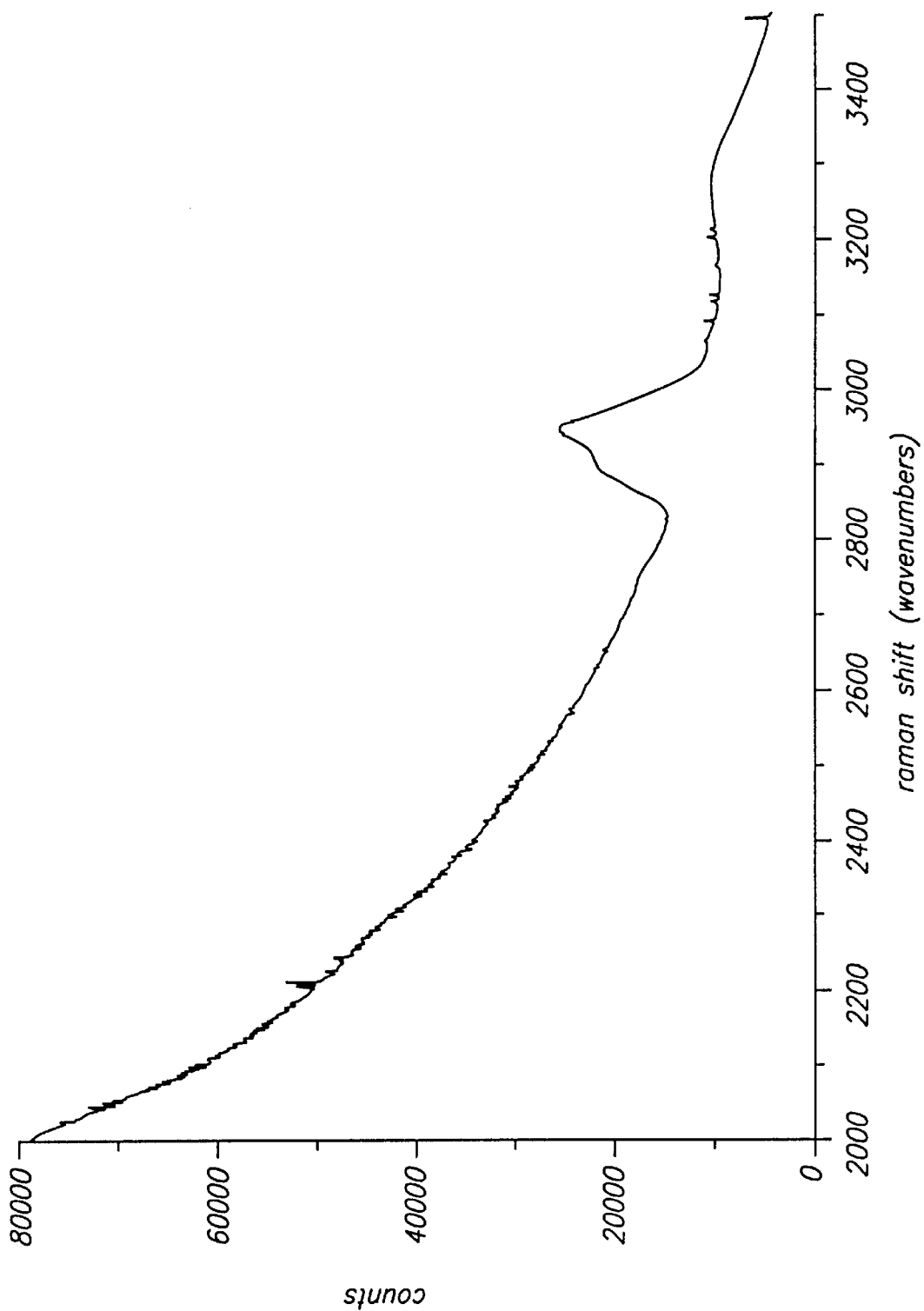
FIG. 5 shows spectra collected from the finger tip following application of cineole and acetone rinsing. Application of this non-deuterated penetrant results in a peak near about 3000 $cm^{-1}$, as would be expected from the C—H bonds of the finger tip.

Raman spectra were collected from a human finger tip irradiated with a near-infrared laser beam using conventional equipment, including a light collection and analysis system. Test agents were applied to the finger tip and allowed to penetrate the tissue for 5 minutes before rinsing the finger tip with acetone. FIG. 3 shows net spectra collected before and after rinsing the finger tip with acetone, in the absence of application of a test agent. FIG. 4 shows spectra collected after application of stearic acid-$d_{35}$, without acetone rinsing. The application of this deuterated form of a substance commonly found in animal fat and soap results in a distinct peak near 2200 cm$^{-1}$. FIG. 5 shows spectra collected from the finger tip following application of cineole and acetone rinsing. Application of this non-deuterated penetrant results in a peak near about 3000, as would be expected from the C—H bonds of the finger tip.

Figure 6:
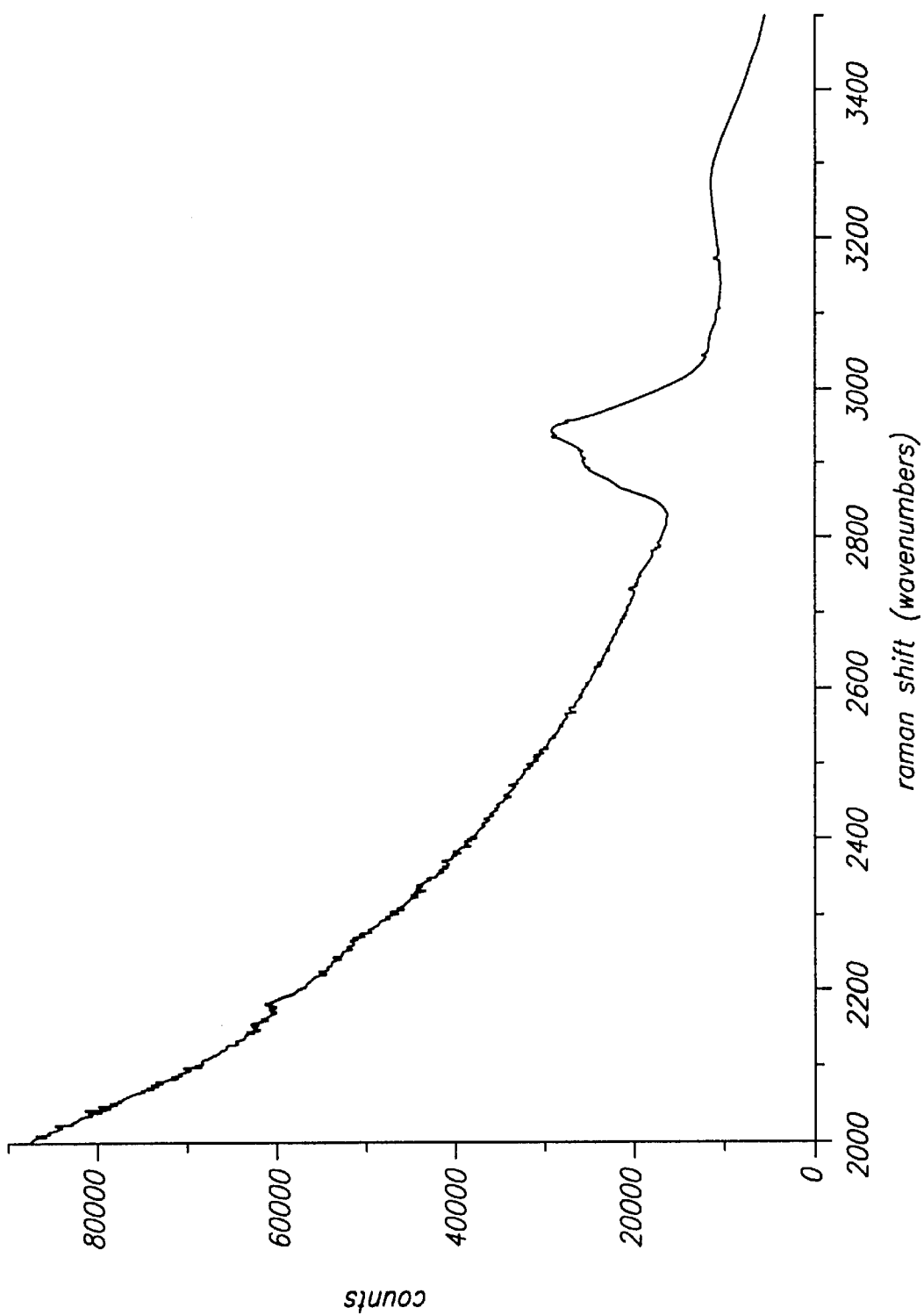
FIG. 6 shows spectra collected after application of cineole with stearic acid-$d_{35}$, and before acetone rinsing. A small peak is observed near 2200 $cm^{-1}$.
Figure 7:
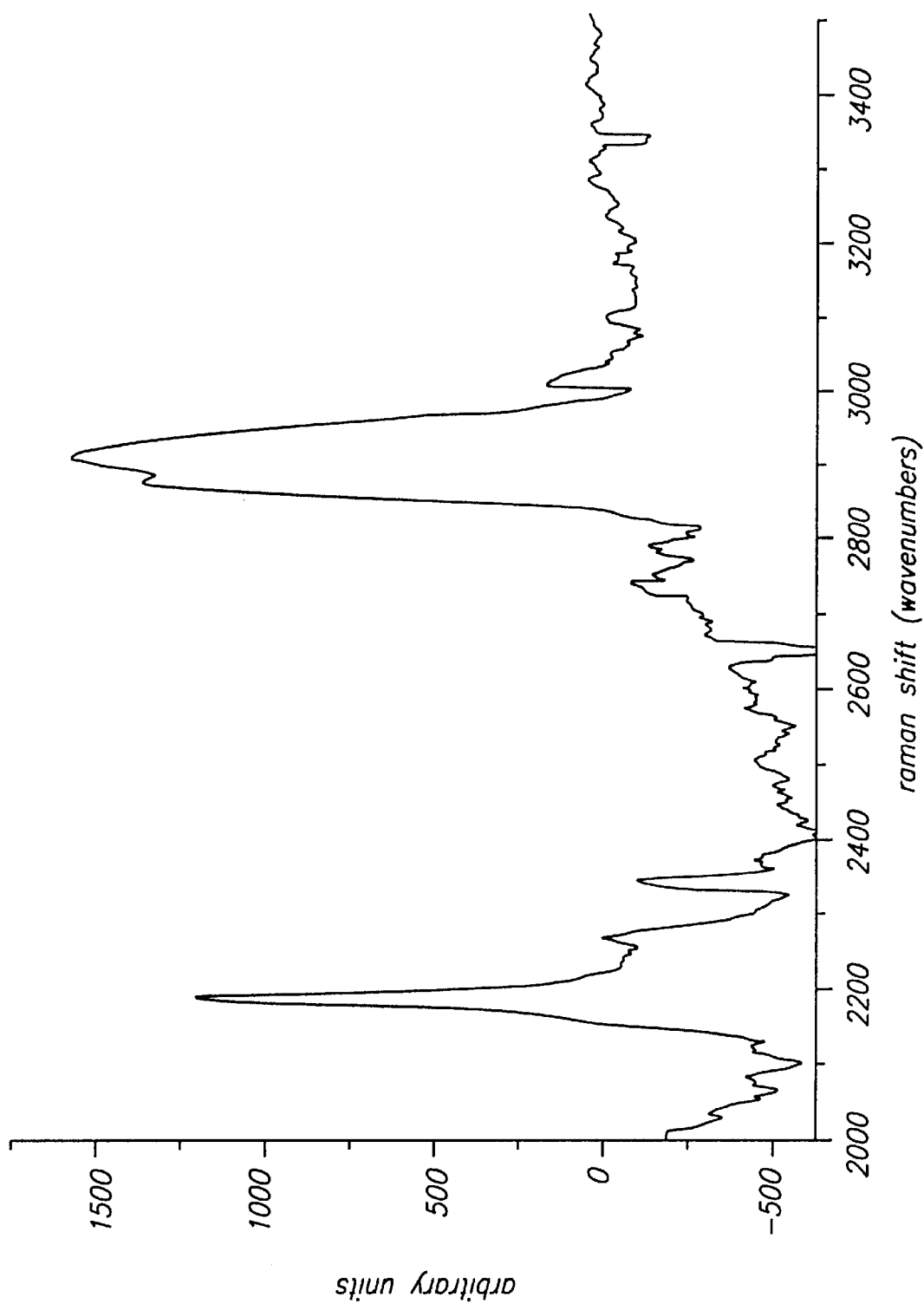
FIG. 7 shows net spectra following application of stearic acid-$d_{35}$ and cineole, before and after acetone rinsing, and reveal a distinct peak near 2200 $cm^{-1}$ as well as near 3000 $cm^{-1}$.
Figure 8:
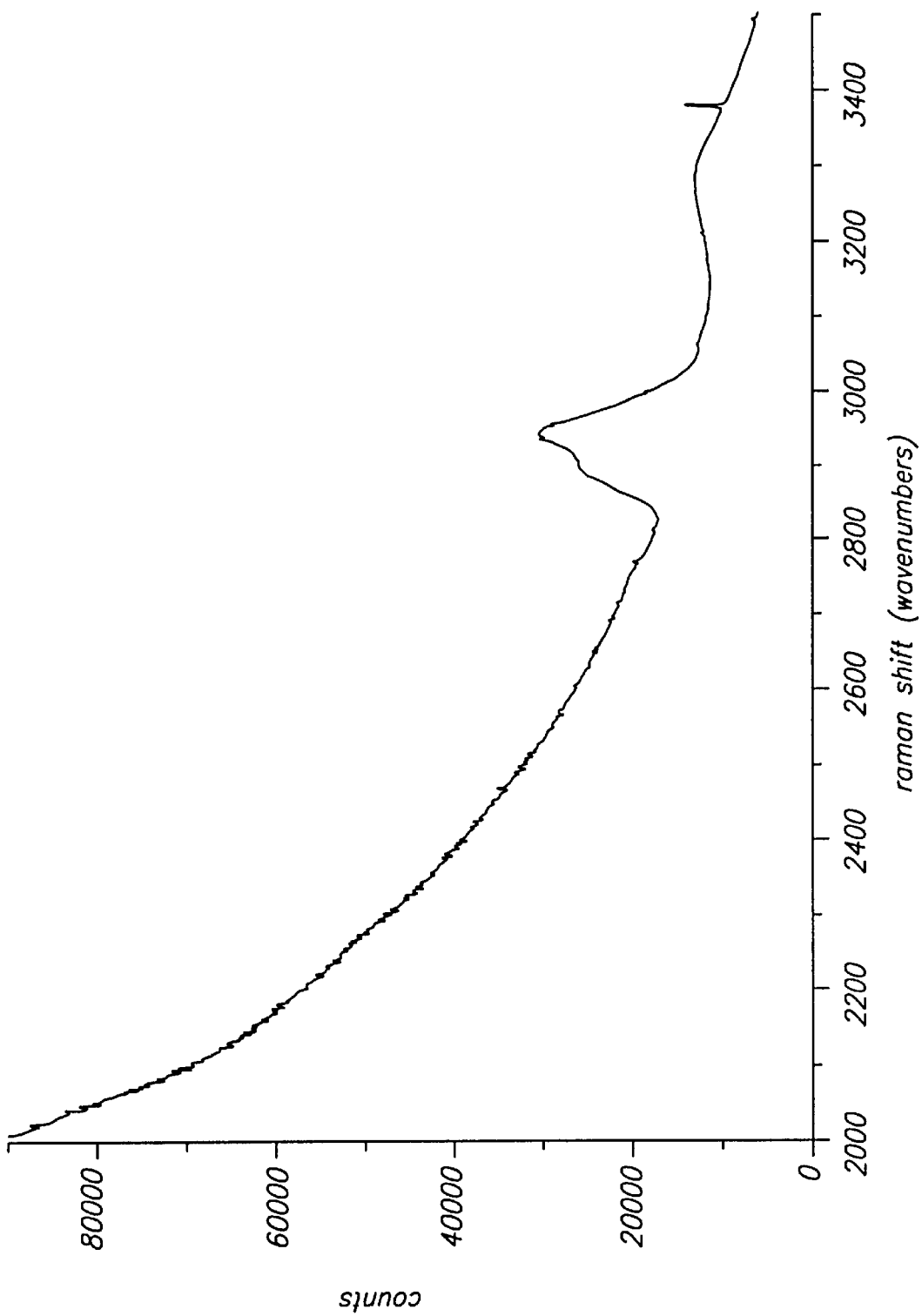
FIG. 8 shows spectra collected as in the preceding figures, following further acetone rinsing.
Figure 9:
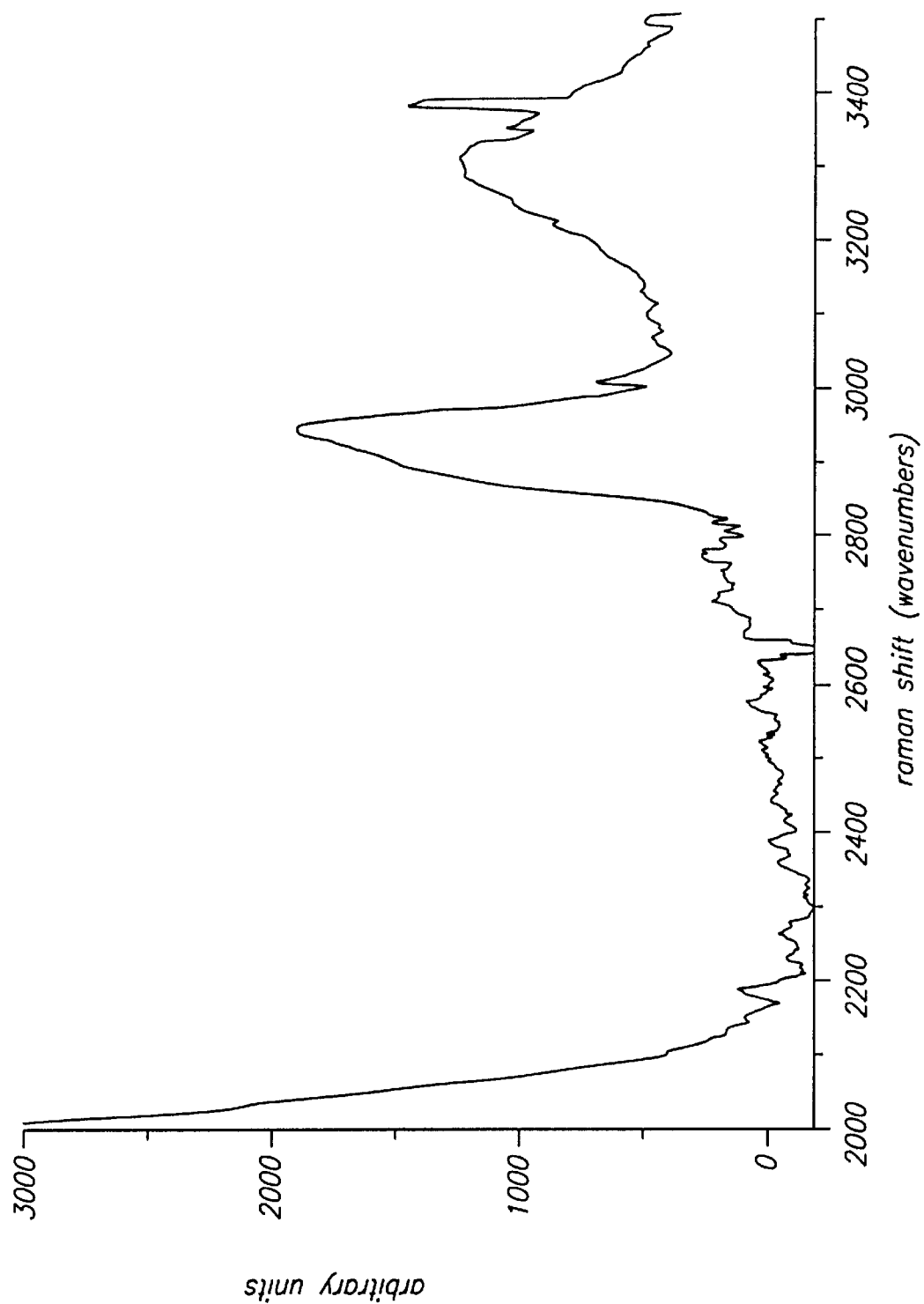
FIG. 9 shows the net spectra, revealing a small peak persisting near 2200 $cm^{-1}$. The persistence of this peak following extensive acetone washing indicates deep penetration (approximately 1–2 mm) of the stearic acid-$d_{35}$.

FIG. 6 shows spectra collected after application of cineole with stearic acid-$d_{35}$, and before acetone rinsing. A small peak is observed near 2200 cm$^{-1}$. The net spectra following application of stearic acid-$d_{35}$ and cineole, before and after acetone rinsing, are shown in FIG. 7 and reveal a distinct peak in the Raman shifted spectra near 2200 cm$^{-1}$ as well as near 3000 cm$^{-1}$. FIG. 8 shows spectra collected following further acetone rinsing, and FIG. 9 shows the net spectra, revealing a small peak persisting near 2200 cm$^{-1}$. The persistence of this peak following extensive washing indicates deep penetration of the stearic acid-$d_{35}$.

These data show that Raman spectra can be obtained and analyzed from skin, and confirm that deuterated imaging agents and, specifically deuterated penetrants, can be used to obtain information about skin at both superficial and deep ($10^2$–$10^3$ microns) levels. The method disclosed herein provides a distinct and easily detected indicator for use in imaging and diagnosis, e.g., a shift in Raman spectra of about 800 cm$^{-1}$.

Example 2

Penetration and Detection of $D_2O$

This example shows the progressive shift in Raman spectra as $D_2O$ penetrates the skin of a human finger tip and exchanges with $H_2O$. These data demonstrate that deuterated imaging agents can be used to observe substances in the aqueous phase (e.g., proteins) as well as the lipid phase (as demonstrated in Example 1).

In this example, Raman spectra were first collected from a dry finger tip. The finger was then immersed in $H_2O$ for 15 minutes, after which the finger was dabbed to dry the skin surface. Raman spectra were collected again for 4 successive intervals of 400 seconds each. The finger was then immersed in $D_2O$ for 15 minutes, after which the finger was dabbed to dry the skin surface. Raman spectra were collected again for 4 successive intervals of 400 seconds each. For each 400 second interval of data collection, the spectra obtained from the dry finger tip, prior to immersion, were subtracted. Then, from the spectra collected during each of the 4 intervals of data collection following immersion in $D_2O$, the spectra collected in the corresponding interval of the series of data collection intervals following $H_2O$ immersion were subtracted. In this manner, the data were normalized to account for effects of wet tissue on the optical propagation in the skin.

Figure 10:
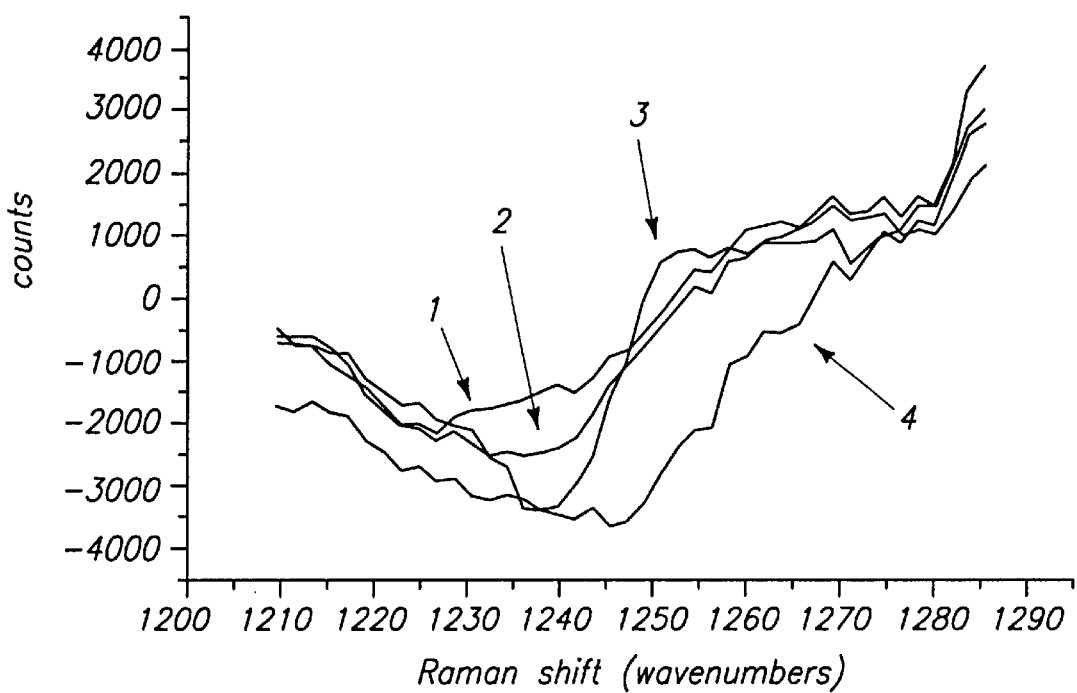
FIG. 10 shows normalized spectral counts near 1240 $cm^{-1}$, collected from a human finger tip at 4 intervals (labeled 1–4, respectively) following a 15 minute immersion in $D_2O$.
Figure 11:
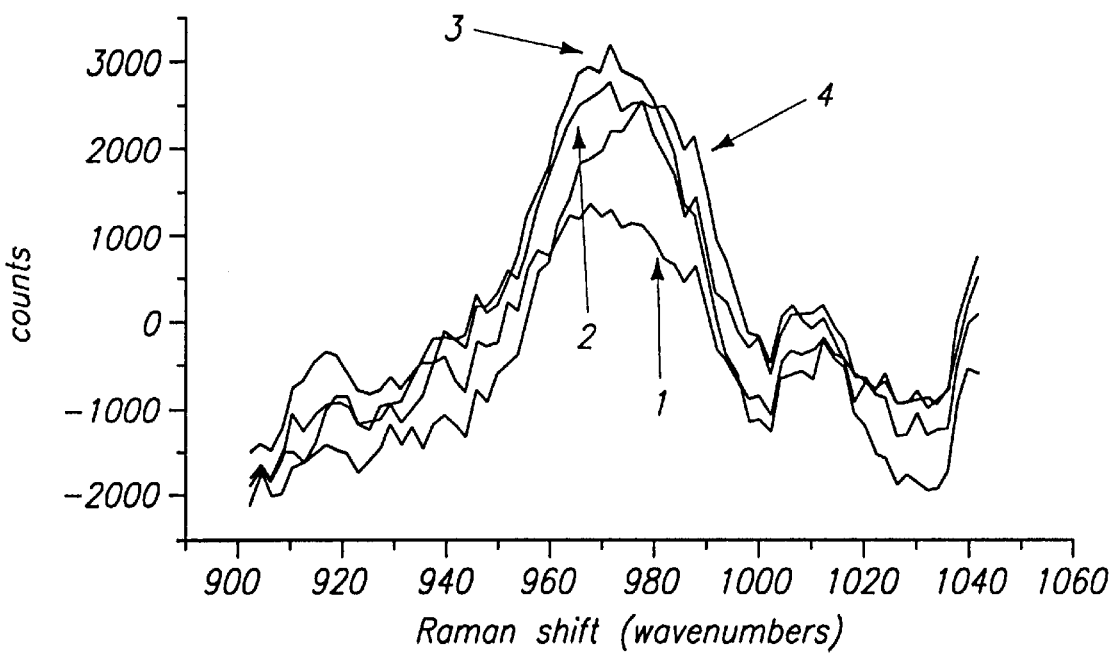
FIG. 11 shows the normalized spectral counts near 970 $cm^{-1}$, collected from a human finger tip at 4 intervals (labeled 1–4, respectively) following a 15 minute immersion in $D_2O$.
Figure 12:
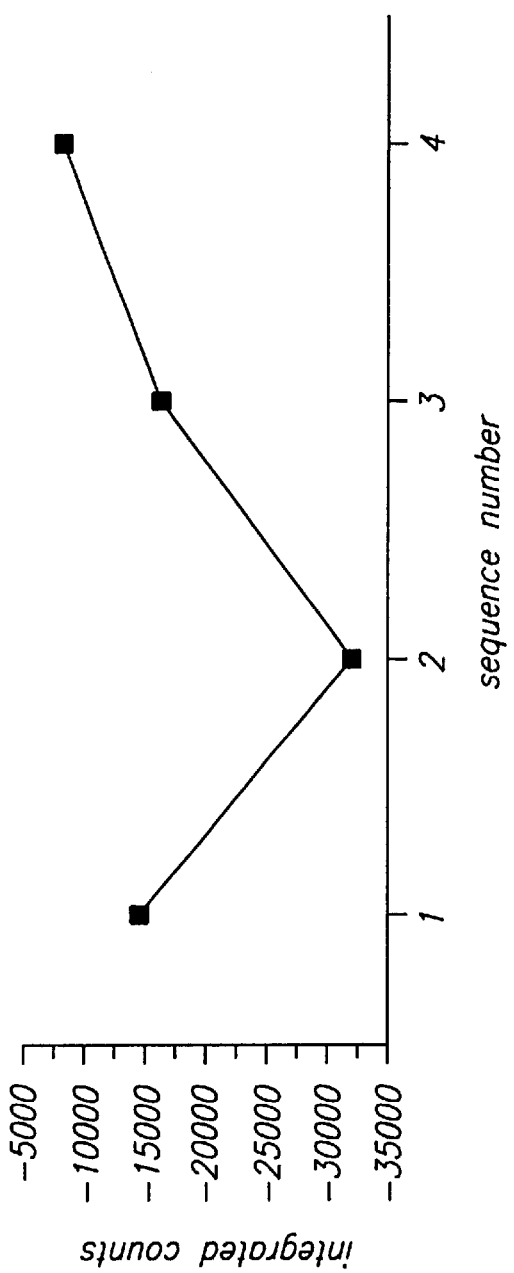
FIG. 12 is a plot of the integrated data for each curve shown in FIG. 10. Data were integrated from 12 $cm^{-1}$ on either side of 1240 $cm^{-1}$.
Figure 13:
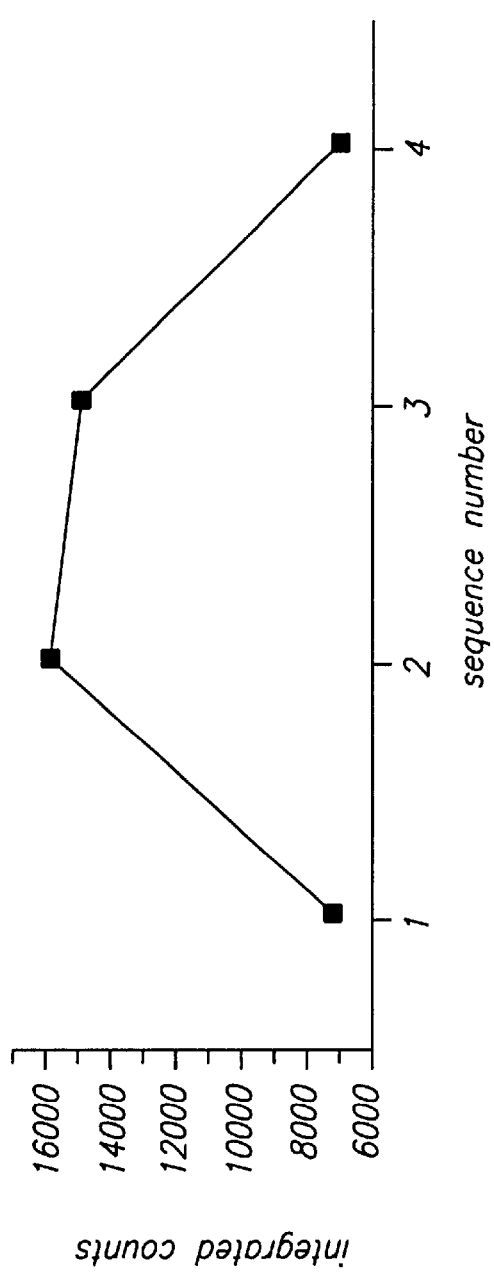
FIG. 13 is a plot of the integrated data for each curve shown in FIG. 11. Data were integrated from 12 $cm^{-1}$ on either side of 970 $cm^{-1}$.

The results are shown in FIGS. 10 and 11, in which "1" indicates the counts obtained at the indicated wavenumbers during the first interval after immersion (following subtraction of spectra collected from the dry finger and then of spectra collected after immersion in $H_2O$, from spectra collected after immersion in $D_2O$). Similarly, "2", "3", and "4" refer to the second through fourth intervals of data collection, respectively. FIG. 10 shows the normalized spectral counts near 1240 cm$^{-1}$, which decrease as the $D_2O$ interacts with the tissue. FIG. 11 shows the normalized spectral counts near 970 cm$^{-1}$, which increase as $D_2O$ exchanges with $H_2O$. FIGS. 12 and 13 show plots of the integrated data for each curve shown in FIGS. 10 and 11, respectively. Data were integrated from 12 cm$^{-1}$ on either side of each peak, 1240 for FIG. 12 and 970 for FIG. 13. These data confirm that, as one species is consumed, the other is formed, and that these changes can be detected by measuring spectral counts.

Those skilled in the art will appreciate other variations and modifications that can be adapted for the methods and apparatus disclosed herein without departing from the spirit and scope of the invention.

What is claimed is:

1. A method for imaging tissue comprising:
   (a) administering to the tissue a deuterated imaging agent;
   (b) irradiating the tissue with a source of electromagnetic radiation; and
   (c) collecting and analyzing Raman spectra emitted from the tissue.

2. The method of claim 1, wherein the deuterated imaging agent comprises an agent that specifically recognizes and binds a target tissue.

3. The method of claim 2, wherein the deuterated imaging agent comprises an antibody or fragment thereof.

4. The method of claim 1, wherein the deuterated imaging agent comprises a highly penetrating deuterated imaging agent.

5. The method of claim 4, wherein the deuterated imaging agent is sufficiently penetrating so as to enhance imaging of voids, such that the agent is detectable in voids after two or more washes.

6. The method of claim 4, wherein the deuterated imaging agent is sufficiently penetrating so as to enhance imaging of densified regions, such that the agent is detectable in densified regions after two or more washes.

7. The method of claim 1, wherein the deuterated imaging agent is capable of selectively penetrating the tissue so as to enhance imaging of a target tissue, such that the agent is detectable in the target tissue after two or more washes.

8. The method of claim 1, wherein the deuterated imaging agent comprises an agent selected from the group consisting of water, phospholipids, alkyl esters, alkyl alcohols, fatty acids, urea and pyrrolidones.

9. The method of claim 1, wherein the deuterated imaging agent comprises an agent selected from the group consisting of partially deuterated and perdeutero-{stearic acid, palmitic acid, linoleic acid, oleic acid, mono-, di-and tri-glycerides, glycerol, cholesterol, propylene glycol, 1–8 cineol, 2-n-nonyl- 1,3-dioxolane), 1-dodecylazacycloheptan-2-one, 4-decycloxazolidin-2-one, sphinganine, 4-hydroxysphinganine, N-acetylated sphinganine and 4-hydroxysphinganine}.

10. The method of claim 1, wherein the analyzing comprises determining a surface fractal dimension of a portion of the tissue having an area and a perimeter.

11. The method of claim 10, wherein the determining of a surface fractal dimension comprises dividing the area of the portion of tissue by the perimeter of the portion of tissue.

12. The method of claim 10, wherein the portion of tissue comprises a cell, a mass of cells or a tumor.

13. The method of claim 10, wherein the surface fractal dimension is derived from first and second iterations of steps (b) and (c) performed with first and second regions of the tissue, respectively, wherein the first region of the tissue comprises a portion of the second region of the tissue.

14. The method of claim 13, wherein the analyzing of step (c) further comprises determining a slope of a line connecting first and second points, wherein the first point is a logarithm of total Raman spectra emitted by the first region of the tissue plotted as a function of a logarithm of area of the first region of the tissue, and the second point is a logarithm of total Raman spectra emitted by the second region of the tissue plotted as a function of a logarithm of area of the second region of the tissue.

15. The method of claim 1, wherein the tissue is living tissue or an excised specimen of tissue.

16. The method of claim 1, that is noninvasive.

17. The method of claim 1, wherein the tissue is human tissue.

18. A diagnostic composition for use with Raman spectroscopic imaging comprising a deuterated imaging agent selected from the group consisting of phospholipids, alkyl esters, alkyl alcohols, and urea, and a pharmaceutically acceptable carrier.

19. The diagnostic composition of claim 18 wherein the deuterated imaging agent is selected from the group consisting of partially deuterated and perdeutero-linoleic acid, oleic acid, mono-, di- and tri-glycerides, glycerol, cholesterol, propylene glycol, 1–8 cineol, 2-n-,nonyl-1,3-dioxolane), 1-dodecylcazacyleoheptan-2-one, 4-decycloxazolidin-2-one, sphinganine, 4-hydroxysphinganine, N-acetylated sphinganine and 4-hydroxysphinganine}.

20. A nonradioactive diagnostic composition for use with Raman spectroscopic imaging comprising a deuterated antibody or fragment thereof.

21. A method for imaging tissue comprising:
   (a) administering to the tissue a deuterated imaging agent;
   (b) irradiating the tissue with a source of electromagnetic radiation; and
   (c) collecting and analyzing spectra emitted from the tissue
wherein the analyzing comprises determining a surface fractal dimension of a portion of the tissue having an area and a perimeter.

22. The method of claim 21, wherein the deuterated imaging agent comprises an agent that specifically recognizes and binds a target tissue.

23. The method of claim 22, wherein the deuterated imaging agent comprises an antibody or fragment thereof.

24. The method of claim 21, wherein the deuterated imaging agent comprises a highly penetrating deuterated imaging agent.

25. The method of claim 24, wherein the deuterated imaging agent is sufficiently penetrating so as to enhance imaging of voids, such that the agent is detectable in voids after two or more washes.

26. The method of claim 24, wherein the deuterated imaging agent is sufficiently penetrating so as to enhance imaging of densified regions, such that the agent is detectable in densified regions after two or more washes.

27. The method of claim wherein 21, the deuterated imaging agent is capable of selectively penetrating the tissue so as to enhance imaging of a target tissue.

28. The method of claim wherein the deuterated imaging agent comprises an agent selected from the group consisting of water, phospholipids, alkyl esters, alkyl alcohols, fatty acids, urea and pyrrolidones.

29. The method of claim 21, wherein the deuterated imaging agent comprises an agent selected from the group consisting of partially deuterated and perdeutero-{stearic acid, palmitic acid, linoleic acid, oleic acid, mono-, di-and tri-glycerides, glycerol, cholesterol, propylene glycol, 1–8 cineol, 2-n-nonyl-1,3-dioxolane), 1-dodecylazacycloheptan-2-one, 4-decycloxazolidin-2-one, sphinganine, 4-hydroxysphinganine, N-acetylated sphinganine and 4-hydroxysphingariune}.

30. The method of claim 21, wherein the determining of a surface fractal dimension comprises dividing the area of the portion of tissue by the perimeter of the portion of tissue.

31. The method of claim 21 wherein the portion of tissue comprises a cell, a mass of cells or a tumor.

32. The method of claim 21, wherein the surface fractal dimension is derived from first and second iterations of steps (b) and (c) performed with first and second regions of the tissue, respectively, wherein the first region of the tissue comprises a portion of the second region of the tissue.

33. The method of claim 32, wherein the analyzing of step (c) further comprises determining a slope of a line connecting first and second points, wherein the first point is a logarithm of total Raman spectra emitted by the first region of the tissue plotted as a function of a logarithm of area of the first region of the tissue, and the second point is a logarithm of total Raman spectra emitted by the second region of the tissue plotted as a function of a logarithm of area of the second region of the tissue.

34. The method of claim 21, wherein the tissue is living tissue or an excised specimen of tissue.

35. The method of claim 21, that is noninvasive.

36. The method of claim 21, wherein the tissue is human tissue.

37. A diagnostic composition for use with Raman spectroscopic imaging consisting essentially of a deuterated imaging agent selected from the group consisting of phospholipids, alkyl esters, alkyl alcohols, and urea, and a pharmaceutically acceptable carrier.

38. The diagnostic composition of claim 37, wherein the deuterated imaging agent is selected from the group consisting of partially deuterated and perdeutero-{linoleic acid, oleic acid, mono-, di-and tri-glycerides, glycerol, cholesterol, propylene glycol, 1–8 cineol, 2-n-nonyl-1,3-dioxolane), 1-dodecylcazacyleoheptan-2-one, 4-decycloxazolidin-2-one, sphinganine, 4-hydroxysphinganine, N-acetylated sphinganine and 4-hydroxysphinganine}.

39. The method of claim 1, wherein the tissue comprises skin.

40. The method of claim 21, wherein tissue comprises skin.

* * * * *

UNITED STATES PATENT AND TRADEMARK OFFICE
CERTIFICATE OF CORRECTION

PATENT NO. : 6,503,478 B2
DATED : January 7, 2003
INVENTOR(S) : Joseph Chaiken and Charles M. Peterson It is certified that error appears in the above-identified patent and that said Letters Patent is hereby corrected as shown below:

<u>Column 17,</u>
Line 35, after "tissue" delete ", such that the agent is"; and
Line 36, delete "detectable in the target tissue after two or more washes".

<u>Column 18,</u>
Line 55, after "claim" insert -- 21, --.

Signed and Sealed this

Nineteenth Day of August, 2003

JAMES E. ROGAN
*Director of the United States Patent and Trademark Office*